United States Patent [19]

Cairns

[11] Patent Number: 4,623,440
[45] Date of Patent: Nov. 18, 1986

[54] ELECTRODE FOR USE IN ELECTROLYTIC CELL

[75] Inventor: John F. Cairns, Cheshire, England

[73] Assignee: Imperial Chemical Industries PLC, London, England

[21] Appl. No.: 760,413

[22] Filed: Jul. 30, 1985

[30] Foreign Application Priority Data

Aug. 16, 1984 [GB] United Kingdom ............... 8420873

[51] Int. Cl.$^4$ .................. C25B 15/00; C25B 11/03; C25B 11/10; G01N 27/30
[52] U.S. Cl. ................................ 204/231; 204/252; 204/254; 204/267; 204/268; 204/284; 204/290 F; 204/292; 204/293
[58] Field of Search ............ 204/231, 284, 435, 290 F, 204/252, 256, 268, 254, 267, 292, 293

[56] References Cited

U.S. PATENT DOCUMENTS

| | | | |
|---|---|---|---|
| 3,291,714 | 12/1966 | Hall et al. ............................ | 204/256 |
| 3,871,985 | 3/1975 | Crippen et al. ..................... | 204/231 |
| 4,163,698 | 8/1979 | Kuo et al. ........................... | 204/435 |
| 4,225,396 | 9/1980 | Graham et al. ..................... | 204/435 |
| 4,502,214 | 3/1985 | Miles et al. ........................ | 204/435 X |

Primary Examiner—Donald R. Valentine
Attorney, Agent, or Firm—Cushman, Darby & Cushman

[57] ABSTRACT

An electrode, for use in an electrolytic cell, which electrode is associated with a reference electrode adjacent to a surface of said electrode, in which the electrode comprises at least two spaced apart members, at least one of which is foraminate and which comprises an operative electrode surface, and in which the reference electrode is positioned between and spaced apart from said members.

A reference electrode may be associated with an anode, and a reference electrode may be associated with a cathode, and the potentials associated with various cell parameters may be monitored, for example over potentials at the anodes and cathodes.

21 Claims, 4 Drawing Figures

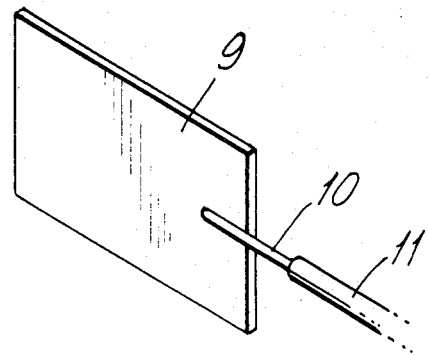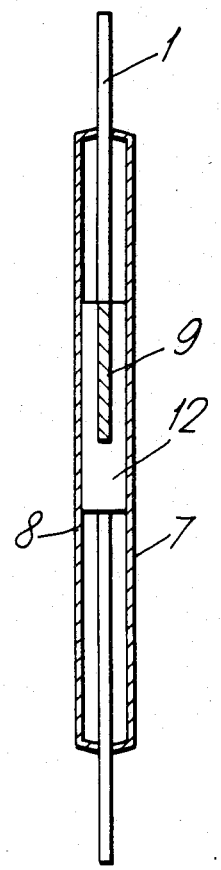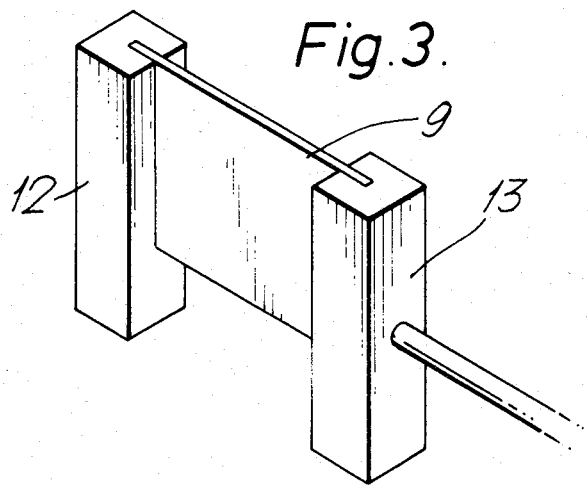

ELECTRODE FOR USE IN ELECTROLYTIC CELL

This invention relates to an electrode for use in an electrolytic cell, and in particular to an electrode associated with a reference electrode for use in an electrolytic cell which reference electrode may be used to monitor the performance of the electrolytic cell.

The voltage at which an electrolytic cell operates is influenced by a number of factors, namely, the theoretical electrolysing voltage, the resistance of the electrolyte which is electrolysed, the resistance of the diaphragm or membrane, if any, positioned between the anode and cathode of the electrolytic cell, the resistance of the metallic conductors and their contact resistances, and the overvoltages at the anode and cathode.

As the cost of electrolysis is proportional to the voltage at which electrolysis is effected, and in view of the high cost of electrical power, it is desirable to maintain the voltage at which an electrolyte is electrolysed to as low a value as possible. It is also desirable to be able to monitor the performance of the component parts of the electrolytic cell, for example to monitor the overvoltages at the anodes and/or at the cathodes of the electrolytic cell, or the potential difference across the diaphragm or membrane in the electrolytic cell, in order that the cause of an increase in voltage of electrolysis may be identified and corrective action taken. For example, where an aqueous solution of an alkali metal chloride is electrolysed gaseous chlorine is evolved at the anode of the electrolytic cell and gaseous hydrogen at the cathode. An overvoltage is associated with the evolution of chlorine at the anode and hydrogen at the cathode and it is desirable to be able to monitor these overvoltages so that, should one or other or both of the overvoltages rise to unacceptable levels, corrective action may be taken.

Overvoltages at such gas-producing electrodes have traditionally been measured by means of a Luggin probe. The Luggin probe consists of a capillary tube which extends into the cell to a position slightly spaced from the electrode the overvoltage at which is to be measured. The capillary tube is connected by a salt bridge to a reference electrode, for example to a calomel reference electrode, located outside the electrolytic cell. The Luggin probe suffers from disadvantages such that it is suitable for use only in obtaining intermittent measurements and is not satisfactory for continuously monitoring the performance of an electrode. In particular it is not suitable for use in monitoring of the performance of an electrode in an electrolytic cell which is operating commercially. Thus, the capillary tube may become blocked by gas which is generated at the electrode when electrolyte is drawn through the capillary tube of the probe, the electrolyte may need to be drawn through the tube by means of a syringe or other suction means in order to have sufficient flow of electrolyte, electrolyte may need to be fed to the cell through the probe from an external reservoir, and the electrolyte to which the reference electrode is exposed may not be identical to the electrolyte which is in contact with the electrode the overvoltage at which is being measured.

In U.S. Pat. No. 4,163,698 there is described an apparatus for measuring the overvoltage at a gas-producing electrode in an electrolytic cell in which aqueous alkali metal chloride solution is electrolysed which is said to overcome the disadvantages associated with the use of a Luggin probe. The U.S. patent describes an in situ reference electrode for measuring the overvoltage at a gas-producing electrode in such an electrolytic cell which comprises a metal tip as the reference electrode immersed in the same electrolyte as the gas-producing electrode and positioned from about 0.2 mm to 1.0 mm away from the gas-producing electrode and within the stream of gas produced by the electrode during electrolysis. The reference electrode is connected by means of an insulated wire to a voltmeter, which is itself also electrically connected to the electrode under test, e.g. to the stem on which the electrode is positioned. The overvoltage at the electrode under test can be determined from the voltmeter reading by correcting for the potential drop in the electrode itself.

In U.S. Pat. No. 4,500,402 there is described an electrolytic cell comprising a foraminate electrode and a wire reference electrode in which the wire reference electrode comprises a lead-in wire portion, a reference wire portion, a sealing material to seal the junction of the lead-in wire and the wire reference portions, in electrolytic cell the reference wire portion extending along and at least partially into a foramen of the foraminate electrode.

The use of such a reference electrodes does, however, suffer from a problem. The operative part of the reference electrodes is a metal tip, or a relatively thin reference wire, which in either case is of very small dimensions, and which is thus capable of measuring the overvoltage only at a small part of the surface of the electrode, namely that part which is positioned opposite to the metal tip or reference wire of the reference electrode. The overvoltage at the electrode may vary over the surface of the electrode and thus the use of a reference electrode having a metal tip or a thin reference wire may give an incorrect measure of the true overvoltage over a substantial part of the surface of the electrode. This problem cannot itself be solved by increasing the size of the reference electrode as the reference electrode may then itself interfere with the electrolysis. The reference electrode is positioned near to one of the electrodes of the electrolytic cell and in the electrical field between the electrodes of the cell. If the reference electrode is of large size it will shield one of the electrodes of the electrolytic cell, e.g. the anode, from the adjacent electrode of the electrolytic cell, e.g. the cathode, and the overvoltage as measured may, for this reason, be incorrect. Moreover, as the reference electrode is placed between the anode and the cathode of the electrolytic cell it will also measure the potential difference in the electrolyte between the reference electrode and the electrode (anode or cathode) under test.

The present invention provides a solution of these problems, and in particular provides a means whereby the performance of an electrolytic cell may be continuously monitored.

According to the present invention there is provided an electrode for use in an electrolytic cell, which electrode is associated with a reference electrode adjacent to a surface of said electrode, characterised in that the electrode comprises two spaced apart members, at least one of which is foraminate and which comprises an operative electrode surface, and in that the reference electrode is positioned between and spaced from said members.

In a further embodiment of the invention there is provided an electrolytic cell which comprises at least one anode and at least one cathode and in which at least one of the anode and cathode comprises an electrode associated with a reference electrode, as herein described.

Both of the anode and the cathode may comprise an electrode associated with a reference electrode, as herein described.

The anode and adjacent cathode of the electrolytic cell may be separated by a separator, which may be a hydraulically permeable porous diaphragm or a substantially hydraulically impermeable ionically permselective membrane.

In the electrolytic cell the foraminate member, or members, of the electrode will face a counter electrode, or electrodes, of opposite polarity. Thus, the reference electrode will be positioned on that side of the foraminate member of the electrode which is remote from the counter electrode ajdacent thereto.

The operative electrode surface is that surface or surfaces of the electrode at which electrolysis takes place and at which gas is evolved during electrolysis where there is a gaseous product of electrolysis.

The electrode may be a bipolar electrode. Thus, one of the members may be a wall member which provides a barrier between the anode and cathode sides of the electrode and which in the electrolytic cell provides a wall which partitions the anode compartment from the cathode compartment. The bipolar electrode may comprise a foraminate member which acts as an anode and which is spaced from the wall and is electrically conductively attached thereto and which comprises an operative anode surface. The bipolar electrode may also comprise a foraminate member which acts as a cathode and which is spaced from the wall on the opposite side thereof from the anode, which is electrically conductively attached to the wall, and which comprises an operative cathode surface. The operative anode and cathode surfaces are spaced away from the wall member of the bipolar electrode and a reference electrode is positioned between and spaced from the wall member and the foraminate anode member, and is thus remote from the operative surfaces of the foraminate anode member, and/or between and spaced from the wall member and the foraminate cathode member, and is thus remote from the operative surface of the foraminate cathode member. In the electrolytic cell the operative surface of an anode of a bipolar electrode will face the operative surface of a cathode of a bipolar electrode adjacent thereto.

The electrode of the present invention may be monopolar and may comprise two spaced apart electrode members at least one of which, and preferably both of which, are foraminate and at least one of which, and preferably both of which, comprise operative electrode surfaces at which electrolysis takes place and at which gas may be evolved during electrolysis. These operative electrode surfaces are spaced apart and are opposite facing and in the electrolytic cell each face a counter electrode. For example, the two operative surfaces of an anode are spaced apart and opposite facing and in the electrolytic cell each face a cathode. Similarly, the two operative surfaces of a cathode are spaced apart and opposite facing and in the electrolytic cell each face an anode. The monopolar electrode is associated with a reference electrode positioned between and spaced from the electrode members, and thus the reference electrode is remote from the operative surfaces of said members.

The electrical field in the electrolytic cell is located between the anodes and adjacent cathodes of the electrolytic cell and, as the reference electrode is positioned remote from the operative electrode surfaces of the anode, or cathode, it is not positioned in the electrical field of the cell, does not shield the anode from the adjacent cathode, nor the cathode from the adjacent anode, and does not interfere with the electrolysis. Thus, the reference electrode may be of relatively large size so that it is capable of determining the overvoltage over a substantial proportion of the operative electrode surface of the electrode with which it is associated.

The reference electrode may be connected by means of an insulated electrical connection, e.g. an insulated wire, to one of the terminals of a D.C. voltmeter, or to other means of measuring electrical potential, positioned outside of the cell, and the other of the terminals may be electrically connected to the electrode with which the reference electrode is associated and which is under test, that is at which the overvoltage is to be measured. This latter electrical connection may, in the case of a monopolar electrode, be to the electrical lead to which the electrode is connected and which is located outside of the cell, and in the case of a bipolar electrode, to a part of the electrode which is under test, which may need to be modified in order to accept the electrical connection. In the electrolytic cell the anode may be associated with such a reference electrode and voltmeter, or the cathode may be associated with such a reference electrode and voltmeter, or both the anode and cathode may be associated with reference electrodes and voltmeters. In this way the overvoltage at the anode, or at the cathode, or at both the anode and at the cathode may be determined directly, after allowance for the small potential drops in the anodes and cathodes themselves.

Alternatively, the reference electrode associated with the anode, and the reference electrode associated with the cathode adjacent to the anode, may be connected by means of separate insulated electrical connections to a D.C. voltmeter positioned outside of the cell. In this way differences in potential across the electrolyte and separator between an anode and adjacent cathode may be measured, and provided the electrolyte concentration, the temperature, and the current density remain constant, this provides a means of monitoring changes in the resistance of the separator. Such changes may be brought about as a result of entrapped gas in the pores of a porous diaphragm, by precipitation of insoluble salts in the pores, or by loss of wettability of the diaphragm. In the case of an ion-exchange membrane such a change in resistance may be brought about by precipitation of insoluble salts within the membrane, by delamination of the membrane where the membrane is made up of a plurality of sheets laminated to each other, or by chemical degradation of the membrane or by the formation of a hole or holes in a membrane.

Thus, the electrode and associated reference electrode, or a plurality of such electrodes and reference electrodes, may be used to monitor several different features of operation of the electrolytic cell, and may be used in such a way that operational problems may be quickly, and specifically, identified. For example, where each anode and cathode in a membrane electrolytic cell is equipped with a reference electrode the electrodes and associated reference electrodes may be used to identify the specific membrane, or membranes, which are not functioning normally, for example, which have been punctured by a hole or holes. These specific membranes can then be replaced.

The operational data produced by the electrode and associated reference electrode may be used to control operation of the electrolytic cell automatically by feeding the data to a suitable control system.

In an alternative manner of electrical connection a voltmeter may be electrically connected as hereinbefore described to the anode and to a reference electrode associated with the anode, and/or a voltmeter may be electrically connected as hereinbefore described to a cathode and to a reference electrode associated with the cathode, and a voltmeter may be electrically connected as hereinbefore described to the reference electrodes associated with the anode and with the cathode. With such an arrangement the overvoltages at the anode and/or the cathode and the voltage associated with the resistance of the electrolyte and the separator may be determined. The same voltmeter may be used with suitable electrical connections and means of switching between electrical connections. Alternatively, separate voltmeters may be used.

It is preferred that the voltmeter be a high impedance voltmeter such that during use gas does not evolve at the surface of the reference electrode. However, a low impedance voltmeter may be used without harmful effect on the reference electrode. The relatively large surface area of the reference electrode enables it to pass a relatively large current without adverse effect on its performance.

The operative electrode surface of at least one of the electrode members must be foraminate so that electrolyte which is in contact with the operative electrode surface may penetrate to the space between the electrode members in which the reference electrode is positioned. It is desirable that the electrolyte in the region of the reference electrode is of substantially the same composition as the electrolyte which is in contact with the operative electrode surfaces of the electrode and for this reason it is preferred that the spacing between the electrode members is not too great. The spacing between the electrode members is preferably not greater than 20 mm, more preferably not greater than 10 mm.

The reference electrode must of course be electrically insulated from the electrode members, in the sense that it must not be in direct contact with either of the electrode members, and it is suitably positioned in a holder of an electrically insulating material which holder is positioned between and in contact with the electrode members.

The electrode may have a variety of different constructions. For example, the foraminate electrode members which comprise the operative electrode surfaces may comprise perforated plates, or meshes. Alternatively, the foraminate electrode members which comprise the operative electrode surfaces may comprise a plurality of longitudinal members which are spaced apart from each other and which lie in a plane. The longitudinal members are preferably parallel to each other and equally spaced from each other.

In the case of a bipolar electrode the electrode may comprise a wall member and a member which comprises a perforated plate, a mesh, or a plurality of longitudinal members positioned on one side, or both sides of the wall member and spaced therefrom and substantially parallel and electrically conductively connected thereto. In the case of a monopolar electrode the electrode may comprise a pair of spaced apart members each in the form of a perforated plate or a mesh, or the electrode may comprise a support member and a plurality of longitudinal members, e.g. strips, substantially parallel to each other and positioned in a plane parallel to and displaced from one face of the support member, and a plurality of strips substantially parallel to each other and positioned in a plane parallel to and displaced from the other face of the support member. The support member may be in the form of a frame to which the longitudinal members, e.g. strips are attached.

The longitudinal members may comprise a plurality of louvres or rods.

The reference electrode may be in the form, for example, of a strip or a plate or a mesh. The reference electrode is suitably planar. The dimensions of the reference electrode are not critical. For example it may have a thickness of the order of up to a few millimeters, e.g. a thickness in the range 0.5 to 3 mm. It is preferred, however, in order that the overvoltage at a substantial area of an electrode may be measured that the reference electrode has a surface area, of one face thereof, of at least 100 sq mm, more preferably at least 200 sq. mm, e.g. up to 1000 sq. mm. By surface area we mean the projected area of the reference electrode and not, for example in the case where the reference electrode is in the form of a mesh, the surface area of the elements of the mesh. The reference electrode may advantageously be positioned substantially equidistantly between the members of the electrode, although equidistant spacing is not necessary. The reference electrode may be held in position by means of a holder of an electrically insulating material which engages with the reference electrode and with the surfaces of the electrode members of the electrode. Holders made of a fluoropolymer, e.g. of polytetrafluoroethylene, are particularly suitable as they have a substantial chemical resistance to many different types of electrolyte, and products of electrolysis, e.g. aqueous alkali metal chloride solution, chlorine, and aqueous alkali metal hydroxide solution.

The materials of construction of the electrodes and of the reference electrode will depend on the nature of the electrolyte in the electrolytic cell. Suitable materials of construction will be described with reference to an electrolytic cell in which an aqueous solution of an alkali metal chloride is to be electrolysed, although it is to be understood that the electrodes and the reference electrode are not limited to the materials of construction suitable for use with this particular electrolyte.

Where aqueous alkali metal chloride solution is to be electrolysed and the electrode is an anode the electrode is suitably made of a film-forming metal or an alloy thereof, for example of zirconium, niobium, tungsten or tantalum, but preferably of titanium, and the operative surfaces of the anode suitably carry a coating of an electro-conducting electrocatalytically-active material. The coating may comprise one or more platinum group metals, that is platinum, rhodium, iridium, ruthenium, osmium or palladium, and/or an oxide of one or more of these metals. The coating of platinum group metal and/or oxide may be present in admixture with, e.g. in the form of a solid solution with, one or more non-noble metal oxides, particularly one or more film-forming metal oxides, e.g. titanium dioxide. Electro-conducting electrocatalytically-active materials for use as anode coatings in an electrolytic cell for the electrolysis of aqueous alkali metal chloride solution, and methods of application of such coatings, are well known in the art. The coating is suitably applied at least to those faces of the anode which in the electrolytic cell face the cathode.

The reference electrode which is associated with the anode may have the same composition as the anode itself and it suitably comprises a substrate of a film-forming metal or alloy thereof and a coating of an electro-conducting electrocatalytically-active material as described.

Where aqueous alkali metal chloride solution is to be electrolysed and the electrode is a cathode the electrode is suitably made of iron or steel, or of other suitable metal, for example nickel or nickel alloy, particularly where the cathode is to be installed in a membrane cell. Nickel or nickel alloy is preferred on account of its corrosion resistance. The operative surfaces of the cathode may be treated, e.g. by roughening the surfaces and/or by coating the surfaces with a suitable material, e.g. a platinum group metal and/or oxide thereof, in order to reduce the hydrogen overvoltage at the cathode. The surface of the cathode so treated is suitably that face of the cathode which in the electrolytic cell faces the anode. The reference electrode which is associated with the cathode may have the same composition as the cathode itself.

The reference electrode may have a composition different from that of the electrode with which it is associated. For example, a reference electrode of platinum or of a platinised metal substrate is suitable for use with both an anode and a cathode.

Where the electrolytic cell is of the hydraulically permeable diaphragm type the aqueous alkali metal chloride solution is charged to the anode compartments of the cell, chlorine which is produced in the electrolysis is removed from the anode compartments of the cell, the alkali metal chloride solution passes through the diaphragms and hydrogen and alkali metal hydroxide produced by electrolysis are removed from the cathode compartments, the alkali metal hydroxide being removed in the form of an aqueous solution of alkali metal chloride and alkali metal hydroxide. Where an aqueous alkali metal chloride solution is electrolysed in an electrolytic cell of the hydraulically impermeable membrane type the solution is charged to the anode compartments of the cell and chlorine produced in the electrolysis and depleted alkali metal chloride solution are removed from the anode compartments, alkali metal ions are transported across the membranes to the cathode compartments of the cell to which water or dilute alkali metal hydroxide solution may be charged, and hydrogen and alkali metal hydroxide solution produced by the reaction of alkali metal ions with water are removed from the cathode compartments of the cell.

Electrolytic cells of the type described may be used particularly in the production of chlorine and sodium hydroxide by the electrolysis of aqueous sodium chloride solution.

Where the separator to be used in the electrolytic cell is a hydraulically permeable diaphragm the nature of the diaphragm will depend on the nature of the electrolyte which is to be electrolysed in the cell. The diaphragm should be resistant to degradation by the electrolyte and by the products of electrolysis and, where an aqueous solution of alkali metal chloride is to be electrolysed, the diaphragm is suitably made of a fluorine-containing polymeric material as such materials are generally resistant to degradation by the chlorine and alkali metal hydroxide produced in the electrolysis. Preferably, the diaphragm is made of polytetrafluoroethylene, although other materials which may be used include, for example, tetrafluoroethylenehexafluoropropylene copolymers, vinylidene fluoride polymers and copolymers, and fluorinated ethylenepropylene copolymers.

Suitable diaphragms are those described, for example, in UK Pat. No. 1503915 in which there is described a microporous diaphragm of polytetrafluoroethylene having a microstructure of nodes interconnected by fibrils, and in UK Pat. No. 1081046 in which there is described a microporous diaphragm produced by extracting a particulate filler from a sheet of polytetrafluoroethylene. Other suitable microporous diaphragms are described in the art.

An asbestos diaphragm may be used.

Where the separator to be used in the cell is an ion-exchange membrane the nature of the membrane will also depend on the nature of the electrolyte which is to be electrolysed in the cell. The membrane should be resistant to degradation by the electrolyte and by the products of electrolysis and, where an aqueous solution of alkali metal chloride is to be electrolysed, the membrane is suitably made of a fluorine-containing polymeric material containing cation-exchange groups, for example, sulphonic acid, carboxylic acid or phosphonic acid groups, or derivatives thereof, or a mixture of two or more such groups.

Suitable cation-exchange membranes are those described, for example, in UK Pat. Nos. 1184321, 1402920, 1406673, 1455070, 1497748, 1497749, 1518387 and 1531068.

In the electrolytic cell in which the electrode of the invention is installed the individual anode compartments of the cell will be provided with means for feeding electrolyte to the compartments, suitably from a common header, and with means for removing products of electrolysis from the compartments. Similarly, the individual cathode compartments of the cell will be provided with means for removing products of electrolysis from the compartments, and optionally with means for feeding water or other fluid to the compartments, suitably from common headers.

The electrode and associated reference electrode of the present invention are not limited in application to any particular type of electrolytic cell. They may be used with a variety of different types of electrolytic cell, but are particularly suitable for use with a filter press type cell comprising a plurality of anodes and cathodes each of which may be associated with a reference electrode.

Where the electrolytic cell is in a substantially steady state operation the reference electrode associated with an anode will take up substantially the reversible potential of the anode reaction, and the reference electrode associated with a cathode will take up substantially the reversible potential of the cathode reaction at the particular conditions prevailing in the electrolytic cell.

A specific embodiment of the invention will now be described with the aid of the following drawings.

FIG. 2 is an isometric view of a reference electrode.

FIG. 3 is an isometric view of a reference electrode and an associated holder.

FIG. 4 is a cross-sectional view of an electrode and a reference electrode and associated holder.

Figure 1:
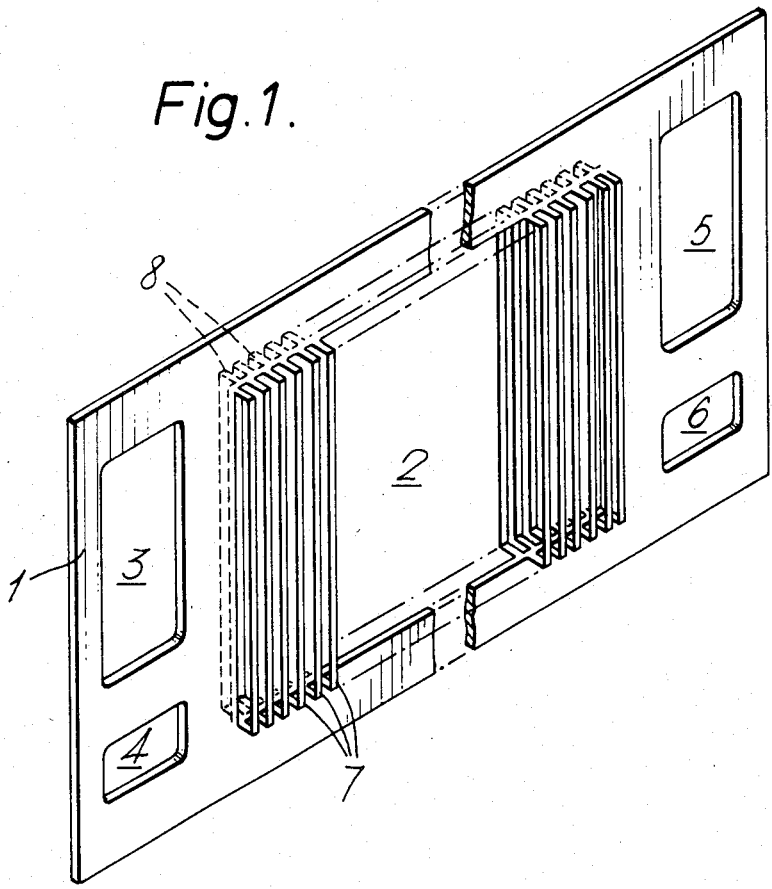
FIG. 1 is an isometric view of an electrode from which, for the sake of clarity, the reference electrode has been omitted.

Referring to FIG. 1 the electrode comprises a planar support member (1) in the form of a frame surrounding a central space (2), and, adjacent to the edges of the frame, a plurality of openings (3, 4, 5, 6) disposed in pairs (3, 4) and (5, 6) near to opposite edges of the frame. These openings (3, 4, 5, 6), when the electrode is assembled into an electrolytic cell, define a part of compartments lengthwise of the cell through which electrolyte and other fluid, e.g. water, may be charged to the electrolytic cell, and through which the products of electrolysis may be removed from the electrolytic cell.

The central opening (2) is bridged by a plurality of strips (7) on one side of the frame and a plurality of strips (8) on the other side of the frame. The strips on each side of the support member (1) are vertically disposed, evenly spaced, and parallel to each other. The strips are offset so that the strips (8) on one side of the support member (1) are positioned opposite to a space between two adjacent strips (7) on the other side of the support member (1). The faces of the strips (7) are in a plane parallel to and laterally displaced from the plane of the support member (1), and similarly the faces of the strips (8) are in a plane parallel to and laterally displaced from the plane of the support member.

The strips may be attached at their ends to the frame of the support member (1) by any suitable means, for example by welding or brazing. Alternatively the strips may be formed by making a plurality of substantially parallel slits in a planar support member (1) and displacing a substantial proportion of each of the strips thereby defined in the support member, alternately first to one side and then to the other side of the support member.

The choice of metal for the metallic part of the electrode will depend on the intended use of the electrode, that is whether the electrode is to be used as an anode or a cathode. Where the electrode is to be used as an anode, for example in an electrolytic cell for the electrolysis of aqueous alkali metal chloride solution, the electrode is suitably made of titanium. Where the electrode is to be used as a cathode in an electrolytic cell for the electrolysis of aqueous alkali metal chloride solution, the electrode is suitably made of iron, e.g. mild steel, but is preferably made of nickel.

Those surfaces of the strips 7 and 8 which in the electrolytic cell are not in contact with an ion-exchange membrane may have a coating of an electrocatalytically active material so that electrolysis takes place at these coated surfaces. The whole of the surfaces of the strips 7 and 8 may have a coating of an electrocatalytically active material.

Referring to FIG. 2, the reference electrode comprises a thin metallic plate (9) to which an electrical lead (10) is attached, the lead 10 being covered by a layer (11) of a corrosion resistant and electrically insulating material for example a layer of a fluoropolymer, e.g. polytetrafluoroethylene. The layer (11) may be shrunk onto the lead (10), and/or a sealant may be placed between the lead (10) and the layer (11), to assist in prevention of ingress liquor into the space between the lead (10) and the layer (11).

Referring to FIG. 3, the metallic plate (9) of the reference electrode is held in position in a pair of holders (12, 13) of a corrosion resistant and electrically insulating material, for example of polytetrafluoroethylene.

The plate (9) of the reference electrode may, for example, be made of titanium where the reference electrode is to be used in combination with an anode for use in an electrolytic cell in which aqueous alkali metal chloride is to be electrolysed. The plate (9) has a coating of an electrocatalytically active material.

The plate (9) of the reference electrode may, for example, be made of nickel, where the reference electrode is to be used in combination with a cathode for use in an electrolytic cell in which aqueous alkali metal chloride is to be electrolysed. The plate (9) has a coating of an electrocatalytically active material.

Referring to FIG. 4, the holders (12, 13 not shown) and the associated plate (9) of the reference electrode are positioned and held between the strips (7, 8) of the electrode.

In operation, the electrical lead (10) of the plate (9) of the reference electrode may be connected to a terminal of a D.C. voltmeter positioned outside of the cell, and another terminal of the voltmeter may be electrically connected to the planar support member (1) of the electrode associated with the reference electrode, for example to a bus-bar to which the planar support member (1) is attached. The overvoltage at the surfaces of the strips (7 and 8) of the electrode may be determined directly.

Alternatively, the electrical lead (10) of the plate (9) of a reference electrode, which is associated with an anode, and the electrical lead (10) of the plate (9) of a reference electrode, which is associated with an adjacent cathode, may be connected to a D.C. voltmeter positioned outside of the cell, in order that changes in voltage between an anode and an adjacent cathode may be determined directly.

Operation of the electrode and associated reference electrode is illustrated in the following example.

EXAMPLE

An electrolytic cell was assembled from the following components

Anode.

An electrode as illustrated in FIG. 1 and consisting of a titanium substrate, the strips 7 and 8 of the electrode being coated with a coating comprising a solid solution of 40 weight % $RuO_2$ and 60 weight % of $SnO_2$.

Cathode.

An electrode as illustrated in FIG. 1 and consisting of a nickel substrate, the surfaces of the strips 7 and 8 of the electrode having been roughened by grit-blasting with 60–80 mesh alumina and being coated with a mixture of platinum and ruthenium and their oxides, the metals being present in a ratio of 25 weight % Pt and 75 weight % Ru.

Membrane.

A laminate of a film of a perfluorinated polymer containing sulphonic acid groups and a film of a perfluorinated polymer containing carboxylic acid groups.

Gaskets.

Gaskets made of EPDM rubber and having a picture frame-like structure and having four openings in the frame thereof equivalent to the openings 3, 4, 5 and 6 in the electrode illustrated in FIG. 1, and also having channels in the walls thereof.

The electrolytic cell was assembled by positioning a gasket on each side of each anode and on each side of each cathode, arranging four anodes and four cathodes alternatively anode-cathode-anode etc. and positioning a membrane between the gaskets associated with each anode and adjacent cathode. The cell was completed by suitable end plates. In the electrolytic cell the openings 3, 4, 5 and 6 in the electrodes, and the corresponding openings in the gaskets, form headers through which aqueous sodium chloride solution, and water or sodium hydroxide solution, may be charged respectively to the anode and cathode compartments of the electrolytic cell via the channels in the walls of the gaskets, and from which aqueous sodium chloride solution and chlorine, and sodium hydroxide solution and hydrogen, respectively, may be removed from the cathode compartments of the cell via the channels in the walls of the gaskets.

Between the strips 7 and 8 of the second and third anodes of the electrolytic cell there was positioned a reference electrode and holder as illustrated in FIGS. 2, 3 and 4, the reference electrode being a 17 mm × 20 mm titanium plate which was coated with the same coating as the anodes.

Between the strips 7 and 8 of the second and third cathodes of the electrolytic cell there was positioned a reference electrode and holder as illustrated in FIGS. 2, 3 and 4, the reference electrode being a 17 mm × 20 mm nickel plate which was coated with the same coating as the cathodes.

These reference electrodes were connected electrically to a high impedance time-averaging voltmeter, as were the second and third anodes and the second and third cathodes of the electrolytic cell. The voltmeter was fitted with switching means which enabled the following voltmeter readings to be determined. (a) Voltmeter reading from anode 2 to the reference electrode associated with anode 2. (b) Voltmeter reading from anode 3 to the reference electrode associated with anode 3. (c) Voltmeter reading from cathode 2 to the reference electrode associated with cathode 2. (d) Voltmeter reading from cathode 3 to the reference electrode associated with cathode 3. (e) Voltmeter reading from reference electrode associated with anode 2 to the reference electrode associated with cathode 2. (f) Voltmeter reading from reference electrode associated with cathode 2 to the reference electrode associated with cathode 3. (g) Voltmeter reading from reference electrode associated with anode 3 to the reference electrode associated with cathode 3.

Electrolysis was effected at an anode current density of 3 kA/m$^2$ and a temperature of 88° C. 310 g/l aqueous sodium chloride solution was charged to the anode compartments and water to the cathode compartments, and chlorine and depleted sodium chloride solution were removed from the anode compartments and hydrogen and sodium hydroxide solution from the cathode compartments. The concentration of sodium hydroxide solution was 33% by weight.

Periodically during operation of the electrolytic cell the voltmeter readings (a) to (g) were determined. The two anodes and the two cathodes and their intervening three membranes constitute a group of three individual electrolytic cells, and the sum of the voltmeter readings a+c+e, c+b+f, and b+d+g constitute the voltages of these individual electrolytic cells.

The observed voltmeter readings are shown in Table 1, experiment A.

It can be seen that there are only very small differences between the electrolytic cell voltages a+c+e, c+b+f, and b+d+g and the electrolytic cell voltage externally determined.

Electrolysis was continued and a small quantity of a soluble iron compound was introduced into the water charged to the cathode compartments of the cell. The resultant voltmeter readings are shown in Table 2, experiment B.

It can be seen that the effect was to increase the voltage of the electrolytic cell, and that this increase was due in large part to an increase in the voltmeter readings c and d, that is the potentials at the cathode of the electrolytic cells.

TABLE 1

| Experiment | Electrolytic cell voltage, volts (externally determined) | Voltmeter readings, volts | | | | | | | Electrolytic cell voltage volts | | |
|---|---|---|---|---|---|---|---|---|---|---|---|
| | | a | b | c | d | e | f | g | (a + c + e) | (c + b + f) | (b + d + g) |
| A | 3.17 | 0.212 | 0.216 | 0.129 | 0.132 | 2.804 | 2.780 | 2.801 | 3.145 | 3.125 | 3.149 |
| B | 3.30 | 0.230 | 0.215 | 0.250 | 0.268 | 2.815 | 2.810 | 2.825 | 3.295 | 3.275 | 3.308 |

I claim:

1. An electrode, for use in an electrolytic cell, which electrode is associated with a reference electrode adjacent to a surface of said first-mentioned electrode, characterised in that said first-mentioned electrode comprises at least two spaced apart members, at least one of which is foraminate and which comprises an operative electrode surface, and in that the reference electrode is in the form of a strip, plate or rod and is positioned between and spaced from said members.

2. An electrode as claimed in claim 1 which is a bipolar electrode characterised in that one of said spaced apart members serves as a wall member which provides a barrier between an anode side and a cathode side of said wall member, in that another of said spaced apart members comprises a foraminate anode member spaced from the wall member and electrically conductively connected thereto and in that the reference electrode is positioned between and spaced from the wall member and the foraminate anode member.

3. An electrode as claimed in claim 1 which is a bipolar electrode characterised in that one of said spaced apart members serves as a wall member which provides a barrier between an anode side and a cathode side of said wall member, in that another of said spaced apart members comprises a foraminate cathode spaced from the wall member and electrically conductively connected thereto, and in that the reference electrode is positioned between and spaced from the wall member and the foraminate cathode member.

4. An electrode as claimed in claim 1 which is a monopolar electrode characterised in that it comprises two spaced apart foraminate electrode members.

5. An electrode as claimed in claim 1 characterised in that the spacing between the electrode members is not greater than 20 mm.

6. An electrode as claimed in claim 1 characterised in that the reference electrode is positioned in a holder of an electrically insulating material and in that the holder is positioned between and in contact with the electrode members.

7. An electrode as claimed in claim 1 characterised in that the foraminate member comprises a perforated plate, a mesh, or a plurality of longitudinal members which are spaced apart from each other and which lie in a plane.

8. An electrode as claimed in claim 1 characterised in that the reference electrode is in the form of a mesh.

9. An electrode as claimed in claim 1 characterised in that the reference electrode has a surface area of one face thereof at least 100 sq. mm.

10. An electrode as claimed in claim 9 characterised in that the reference electrode has a surface area in the range 200 sq. mm. to 1000 sq. mm.

11. An electrode as claimed in claim 1 characterised in that the electrode is an anode and is made of a film-forming metal having a coating of an electroconducting electrocatalytically-active material.

12. An electrode as claimed in claim 1 characterised in that the electrode is a cathode and is made of nickel or nickel alloy.

13. An electrode as claimed in claim 11 characterised in that the reference electrode is associated with an anode and is made of a film-forming metal having a coating of an electroconducting electrocatalytically-active material.

14. An electrode as claimed in claim 12 characterised in that the reference electrode is associated with a cathode and is made of nickel or nickel alloy.

15. An electrolytic cell which comprises at least one anode and at least one cathode characterised in that at least one of the anode and cathode comprises an electrode associated with a reference electrode as claimed in claim 12.

16. An electrolytic cell as claimed in claim 15 which comprises at least one anode and at least one cathode characterised in that both the anode and cathode comprise an electrode associated with a reference electrode as claimed in claim 1.

17. An electrolytic cell as claimed in claim 15 characterised in that the anode and adjacent cathode are separated by a hydraulically permeable porous diaphragm or a substantially hydraulically permeable ionically permselective membrane.

18. An electrolytic cell as claimed in claim 15 characterised in that the reference electrode is connected by means of an insulated electrical connection to a D.C. voltmeter or to other means of measuring electrical potential and in that the electrode associated with the reference electrode is electrically connected to the D.C. voltmeter or to other means of measuring electrical potential.

19. An electrolytic cell as claimed in claim 18 characterised in that both the anode and associated reference electrode and the cathode and associated reference electrode are connected to a D.C. voltmeter or to other means of measuring electrical potential.

20. An electrode as claimed in claim 19 characterised in that reference electrode associated with the anode and the reference electrode associated with the cathode are electrically connected to a D.C. voltmeter or other means of measuring electrical potential.

21. An electrolytic cell as claimed claim 15 characterised in that the electrolytic cell comprises a plurality of anodes and cathodes each of which is associated with a reference electrode.

* * * * *